US009157063B2

(12) United States Patent
Prien et al.

(10) Patent No.: US 9,157,063 B2
(45) Date of Patent: Oct. 13, 2015

(54) METHOD AND APPARATUS FOR GENDER SELECTION BASED ON PH

(75) Inventors: Samuel D. Prien, Shallowater, TX (US); Lindsay L. Penrose, Olney, TX (US)

(73) Assignee: Texas Tech University System, Lubbock, TX (US)

( * ) Notice: Subject to any disclaimer, the term of this patent is extended or adjusted under 35 U.S.C. 154(b) by 1627 days.

(21) Appl. No.: 12/523,430

(22) PCT Filed: Oct. 31, 2007

(86) PCT No.: PCT/US2007/083235
§ 371 (c)(1),
(2), (4) Date: Feb. 2, 2010

(87) PCT Pub. No.: WO2008/088601
PCT Pub. Date: Jul. 24, 2008

(65) Prior Publication Data
US 2010/0144030 A1    Jun. 10, 2010

Related U.S. Application Data

(60) Provisional application No. 60/885,045, filed on Jan. 16, 2007.

(51) Int. Cl.
C12N 5/071    (2010.01)

(52) U.S. Cl.
CPC ............................ C12N 5/0612 (2013.01)

(58) Field of Classification Search
CPC ................................................. C12N 5/0612
USPC ............................................................. 435/325
See application file for complete search history.

(56) References Cited

U.S. PATENT DOCUMENTS

| 4,083,957 A * | 4/1978 | Lang ................................. 435/30 |
| 4,225,405 A | 9/1980 | Lawson |
| 5,346,990 A | 9/1994 | Spaulding |
| 6,391,654 B1 * | 5/2002 | Bateman ........................ 436/518 |
| 6,489,092 B1 | 12/2002 | Benjamin et al. |
| 6,709,675 B1 | 3/2004 | Lombardin et al. |
| 6,818,018 B1 | 11/2004 | Sawhney |
| 6,838,449 B2 | 1/2005 | Asgharian |
| 7,179,641 B2 | 2/2007 | Brickwood |
| 7,195,920 B2 | 3/2007 | Seidel et al. |
| 2004/0091397 A1 | 5/2004 | Picard |
| 2007/0190653 A1 * | 8/2007 | Heinrich ........................ 435/345 |

FOREIGN PATENT DOCUMENTS

WO    2004/072220 A2    8/2004

OTHER PUBLICATIONS

Extended European Search Report for EP 07 87 1320 dated Feb. 23, 2010.

Bowden, C., et al., "Use of a cell strainer to facilitate processing human semen samples for Intrauterine Insemination (IUI)," Fertility and Sterility (2003), 80:S296 (abstract).
Diasio, R. B., et al., "Effects of pH on the Migration of X and Y Sperm," Fertility and Sterility (1971), 22:303-305.
Garner, D. L., "Flow cytometric sexing of mammalian sperm," Theriogenology (2006), 65:943-957.
Johnson, L. A., "Sexing mammalian sperm for production of offspring: the state-of-the-art," Animal Reproduction Science (2000), 60-61:93-107.
Muehleis, P. M., et al., "The effects of altering the pH of seminal fluid on the sex ratio of rabbit offspring," Fertility and Sterility (1976), 27:14-88-1495.
Pratt, N. C., et al., "Offspring sex ratio in hamsters is correlated with vaginal pH at certain times of mating," Behavorial and Neural Biology (1987), 48:310-316.
Penrose, L. L., et al., "A preparatory technique for semen selection," Fertility and Sterlility (2008), 90:S416-417.
Ingermann, et al., "Carbon dioxide and pH affect sperm motility of white sturgeon (Acipenser transmontanus)," The Journal of Experimental Biology, (2002) 205:2885-2890.
Maxwell, WMC, et al., "Integration of Sperm Sexing Technology into ART Toolbox," Anim. Reprod. Sci. Jul. 2004;82-83:79-95.
Rens, W., et al., "An X-Y Paint Set and Sperm FISH Protocol that can be Used for Validation of Cattle Sperm Separation Procedures," Reproduction (2001) 121:541-546.
Blecher, S.R., et al., "A New Approach to Immunological Sexing of Sperm," Theriogenology 52:1309-1321 (1999).
Dolz, M., et al., "A Time-Dependent Expression for Thixotropic Areas. Application to Aerosil 200 Hydrogels," J Pharm Sci 89:790-797 (2000).
Downing, D.C., et al., "The Effect of Ion-Exchange Column Chromatography on Separation of X and Y Chromosome-Bearing Human Spermatozoa," Fertil. Steril. 27:1187-1190 (1976).
Hossain, A.M., et al., "Preconceptional Sex Selection: Past, Present and Future," Arch. Androl. 40:3-14 (1998).
Johnson, L.A, et al., "Recent Avances in Sex Preselection of Cattle: Flow Cytometric Sorting of X- and Y-Chromosome Bearing Sperm Based on DNA to Produce Progeny," Theriogenology 41:51-56 (1994).

(Continued)

*Primary Examiner* — Taeyoon Kim
*Assistant Examiner* — Tiffany Gough
(74) *Attorney, Agent, or Firm* — Chainey P. Singleton; Edwin S. Flores; Chalker Flores, LLP

(57) ABSTRACT

The present invention includes methods and apparatus to separate X or Y-chromosome bearing sperm cells in a population by first placing the population of sperm cells at physiological pH environment, and simultaneously contacting the population of sperm cells with one or more additional sub-environments with different pH values. The exposure allows mobile sperm cells bearing X or Y-chromosome to migrate to the different pH sub-environments, wherein each cell only exposed or come in contact with one pH sub-environment. Finally, the collecting X or Y-chromosome enriched population of sperm cells is performed.

9 Claims, 8 Drawing Sheets

(56) References Cited

OTHER PUBLICATIONS

Johnson, L.A., "Sex Preselection by Flow Cytometric Separation of X and Y Chromosome-bearing Sperm Based on DNA Difference: a Review," Reprod. Fertil. Dev. 7:893-903 (1995).

Kawarasaki, T., et al., "Rapid and Simultaneous Detection of Chromosome Y- and 1-Bearing Porcine Spermatozoa by Fluorescence in Situ Hybridization," Molecular Reproduction and Development 43:548-553 (1996).

Kobayashi, J., et al., "Fluorescence in Situ Hybridization with Y Chromosome-Specific Probe in Decondensed Bovine Spermatozoa," Theriogenology 52:1043-1054 (1999).

Prien, S.D., "A Comparative Study of Calcium Utilization in Human and Porcine Spermatozoa," PhD Diss., Texas Tech University, Lubbock, Tx. (1991).

Stolkowski, J., Choukroun, J., "Preconception Selection of Sex in Man," Isr. J. Med. Sci. 17:1061-1067 (1981).

* cited by examiner

METHOD AND APPARATUS FOR GENDER SELECTION BASED ON PH

TECHNICAL FIELD OF THE INVENTION

The present invention relates in general to the field of gender selection, and more particularly, the present invention relates to a method and an apparatus for numerically enhance semen populations with cells of one sex as to increase the chances of having an offspring of the desired sex.

BACKGROUND OF THE INVENTION

Without limiting the scope of the invention, its background is described in connection with method and apparatus for gender selection.

When thinking of conceiving an offspring, most people often have a preference for a child having a particular gender. However, it is difficult to select or even influence the selection of the gender of an as yet not conceived offspring as many factors influence natural gender selection in human or other animal.

It has been known for years that gender, in mammals, is determined by the presence of XX chromosomes in females or one X chromosome and one Y chromosome in males (XY). Joining of sperm and egg during the fertilization process results in a zygote containing one chromosome from the female and one chromosome from the male. Only one type of egg results from the female, an egg containing a single X chromosome. But two types of sperm result from the male, one carrying a single X chromosome and one carrying a single Y chromosome. Since these two types of sperm are produced in almost equal numbers there is basically a 50-50 chance of conceiving one gender or the other if all other factors are equal since fertilization of an egg by an X-bearing sperm will lead to an XX zygote while fertilization of an egg by a sperm with a Y chromosome will lead to an XY zygote.

There are number of reasons for performing gender selection. Economically, gender selection can be seen in the dairy industry which prefers one sex in its livestock production system in order to increase management efficiency and productivity. Research in gender selection is an ongoing effort in the field of art, and many methods have been attempted to achieve the separation of X- and Y-chromosome bearing sperm.

For example, in the U.S. Pat. No. 5,346,990 titled "Sex-associated membrane proteins and methods for increasing the probability that offspring will be of a desired sex", Spaulding described a method of sorting living cells based on DNA content. Here, mammalian sperm subpopulations enriched in X- or Y-sperm, e.g., X- and Y-enriched sperm-plasma-membrane vesicles. Substantially pure sex-associated membrane (SAM) proteins. Antibodies binding to X- or Y-SAM proteins, essentially free of antibodies binding to Y—or X-SAM proteins respectively, or to the H—Y antigen. Semen samples enriched for X- or Y-sperm. To obtain the population, a refined X sex-associated membrane protein is characterized by a higher band density on an SDS/PAGE of plasma membrane proteins prepared from X-enriched sperm subpopulations as compared to the corresponding band density on an SDS/PAGE of plasma membrane proteins prepared from whole sperm or prepared from Y-enriched sperm subpopulations; or a refined Y sex-associated membrane protein characterized by a higher band density on an SDS/PAGE of plasma membrane proteins prepared from Y-enriched sperm subpopulations as compared to the corresponding band density on an SDS/PAGE of plasma membrane proteins prepared from whole sperm or prepared from X-enriched sperm subpopulations.

Another example can be found in the U.S. Pat. No. 6,489,092 titled "Method for sex determination of mammalian offspring". Briefly, a method for increasing the percentage of mammalian offspring of either sex which comprises contacting a semen sample with an antibody specific for the spermatozoa determinative of one sex and separating the spermatozoa from spermatozoa determinative of the other sex, the antibody being bound to a non-porous magnetic bead support having a diameter of 0.1 to 2 microns is taught.

Yet another example can be found in the U.S. Pat. No. 7,195,920. The '920 patent describes collection systems for cytometer sorting of sperm. This patent describes an improved flow cytometer system particularly adapted to use for sex-selected sperm sorting include enhanced sheath fluid and other strategies which minimize stress on the sperm cells, including a 2.9 percent sodium citrate sheath solution for bovine species and a HEPES bovine gamete media for equine species. Improved collection systems and techniques for the process are described in the '920 patent so that commercial applications of sperms samples as well as the resulting animals may be achieved.

Although techniques exist in the field to sort sperm cells bearing X or Y chromosome, all existing methods, save the flow cytometry method, have had only limited clinical or statistical success in controlling the sex of offspring. Further, the cytometry method, while fuctional, has a high cost, require expensive equipment and highly skilled technicians to operate and has the potential of induction of mutations. The present inventors recognize the limitation in the existing art and the desire to achieve sex-sorted sperm samples using inexpensive disposable components and substances.

SUMMARY OF THE INVENTION

The present invention is to provide methods and apparatus for separating sperm cells having X or Y chromosome. In certain embodiments, the present invention describes methods to separate X or Y-chromosome bearing sperm cells in a population by first placing the population of sperm cells at physiological pH environment, and simultaneously contacting the population of sperm cells with one or more additional sub-environments with different pH values. The exposure allows mobile sperm cells bearing X or Y-chromosome to migrate to the different pH sub-environments, wherein each cell only exposed or come in contact with one pH sub-environment. Finally, the collecting X or Y-chromosome enriched population of sperm cells is performed.

In another embodiment, the present invention describes an apparatus for increasing the proportion of X or Y-chromosome bearing sperm cells in a population. The apparatus typically is one or more container, wherein the container comprises at least one main chamber; and one or more sub-chambers. The main chamber and sub-chambers are typically separated by a biocompatible mesh material that has a pore size of about 40-70 μm. The biocompatible mesh material may permit sufficient minor exchange of ions significant enough to permit mobility pathways for sperm cells. The biocompatible mesh material also may prevent mass flow of fluid between main chamber and sub-chambers, but allows free movement of sperm cells and slow movement of fluids between chambers.

In yet another embodiment, the present invention describes the creation of an overall environment that presents each sperm cell with several sub-environments simultaneously allowing each sperm cell to migrate to its preferred location. The sub-environment is created by a chambered dish which has a bio-compatible cell sifting basket, or equivalent mesh material seeded in the middle effectively creating a main chamber and one or more sub-chambers. Each sub-chamber of the system may be filled with a bio-compatible media of a pre-determined pH. The charge of the mesh and static pressure initially prevent movement of solutions thru the mesh. The size of the mesh opening will be of sufficient size to allow the passage of sperm cells of the specie being sorted, for example, but not limited to 40~70 μm. The center chamber is filled with a mixture of a biocompatible media of a predetermined pH and processed semen from a selected male. Filling of the center chamber will allow for minor exchange of ions between each of the sub-chambers and the center chamber described. The ion exchange will be sufficient to create pathways to attract cells to a preferred sub-environment; sperm cells will be attracted to one of the presented sub-environments. Most importantly, the design of the system does not require that cells migrate through suboptimal environments before arriving at the sub-environment of choice.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
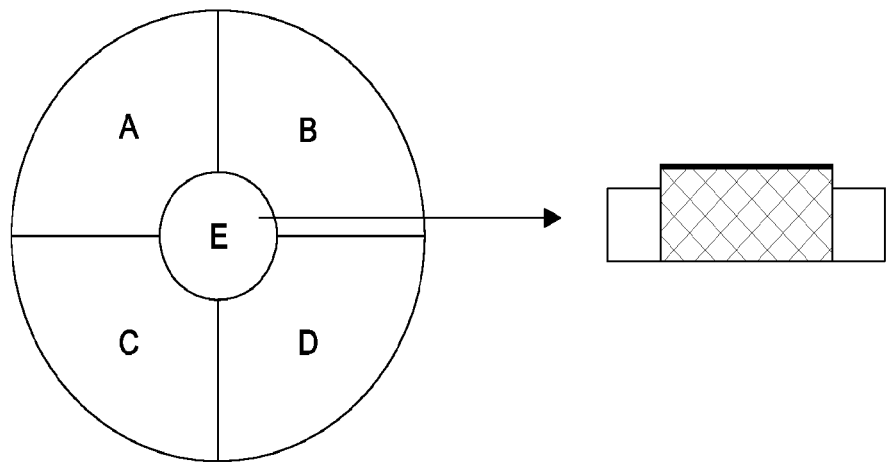
FIG. 1 is a schematic diagram of the Texas Tech University Semen Separation Chamber with a top view (left) and a cut-away side view (right).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "biocompatible" refer to a material that does not have toxic or injurious effects on semen or other biological systems. Suitable materials for use with the method and apparatus of the present invention include those approved for medical applications that involve contact with internal body fluids, e.g., those that meet US PV1 or ISO 10993 standards. Generally, the materials will not degrade substantially, e.g., due to exposure to solvents during at least a single use. The materials are typically sterilized using, e.g., radiation or ethylene oxide (EtO) sterilization. Suitable materials include extrudable materials (or materials that are coated therewith), including, but are not limited to, nylon, polypropylene, polycarbonate, acrylic, polysulphone, polyvinylidene fluoride (PVDF), fluoroelastomers (e.g., VITON, available from DuPont Dow Elastomers L.L.C.), thermoplastic elastomers (e.g., SANTOPRENE, available from Monsanto), polyurethane, polyvinyl chloride (PVC), polytetrafluoroethylene (PTFE), polyphenylene ether (PFE), perfluoroalkoxy copolymer (PFA) (e.g., TEFLON PFA from E.I. du Pont de Nemours and Company), and combinations thereof.

As used herein, the term "thixotropic" is used to describe one or more agents, e.g., certain gels, which liquefy when subjected to vibratory forces like simple shaking, and then solidify again when left standing. Thixotropic behavior is observed when long-chain molecules tend to orient themselves in the direction of flow; as the applied force is increased, the resistance to flow is decreased. Yet when high shear stress is removed, the solution will quickly revert to its original viscous state. Some celluloses exhibit thixotropic behavior wherein the solution returns to its viscous state over a period of time. Examples of thixotropic agents for use with, e.g., food, pharmaceuticals, are well known in the art, e.g., "A time-dependent expression for thixotropic areas. Application to Aerosil 200 hydrogels," M. Dolz, F. González, J. Delegido, M. J. Hernández, J. Pellicer, J. Pharm. Sci., Vol. 89, No. 6, pages 790-797 (2000), relevant portions incorporated herein by reference. Numerous examples of thixotropic agents, such as cellulose (e.g., carboxymethylcellulose), gums (e.g., xanthan), collagen, gelatin, aerogels and others are well known in the art and may be used with the present invention, e.g., U.S. Pat. Nos. 6,709,675; 6,838,449; 6,818,018, relevant portions incorporated herein by reference.

The desire to control the gender can be seen across time and culture, from the nobility of medieval Europe striving for male heirs to modern day dairy farmers seeking female calves to increase productivity in their herds; there are many motivations driving people to discover a practical technique to control sex. One classical example of a livestock production system that prefers one sex to the other is the dairy industry, whose product is exclusively based on the female of the species. For this reason the dairy industry would benefit from the ability to sex sort semen and thereby limiting the number of bull calves born each year. Further, dairymen could increase their heifer calf crop each year allowing them to select the very best heifers to be the next generation of milk producers. Additionally, producers could increase the size of their milking herd without the added expense of purchasing cows from external sources. Beyond the advantages of an increased heifer crop, the dairy producer would have the ability to reduce or completely eliminate the management practices necessary to raise and wean a dairy bull calf either for the veal market or to eventually become a sire.

The present invention improves upon the techniques to sort sperm cells bearing X or Y chromosome, because all existing methods have had only limited clinical or statistical success in controlling the sex of offspring or have proven too expensive for routine use (flow cytometry). In addition to high cost, flow cytometry has the potential of induction of mutations further cast shadow of doubt on the existing techniques. The present invention addressed the limitations in the existing art and achieves an improved sex-sorted sperm samples using inexpensive disposable components and substances.

One existing method for sex selection of sperm has revolved around the pH environment of cells in the reproductive tract. It has been commonly theorized that different pHs would affect the viability and motility of the differing sperm populations directly impacting the sex of the offspring. Some claimed that more male offspring were conceived if the cervical fluids were alkaline and that female offspring were selected when cervical mucus is acidic. These claims supported by anecdotal recommendations which include the timing of coitus in relation to ovulation when the pH of the female reproductive tract shifts from acidic to alkaline and douching with a vinegar or baking soda solution to influence the sex of the offspring. [1]

An alternative technique from an incubation step in an altered pH buffer is the use of a pH gradient, allowing the sperm cells to migrate toward their favored environment. Diasio and Glass studied the migration of human spermatozoa into capillary tubes containing pH adjusted Tyrode's solution. [2] To determine the chromosomal complement of the migrated sperm cells, slides were prepared and stained using quinacrine dihydrochloride and quinacrine mustard to selectively stain the long arm of the Y-chromosome. However, this study showed no difference in the percentage of Y-chromosomes detected regardless of the pH media used. Downing et al. examined the use of a resin ion exchange column to separate semen. The resins were of different pH strengths utilizing either sodium or chloride ions as the exchange group. Human and rabbit semen samples were layered on top of the resin packed in a chromatography column and allowed to flow through the column. After staining for F-bodies it was determined that there was no difference in the concentration of Y-bearing spermatozoa regardless of the strength of the ion used.

There is a common thread through all of these pH techniques; sperm cells are being asked to travel through many less than optimal environments to "find" the environment that will best support them. These techniques are therefore based upon sperm randomly interacting with a preferred environment. Further, a number of the environments presented might be detrimental to sperm motility and viability.

Gender selection has advantages that can be realized in other branches of animal production. As profit margins tighten, the ability to influence pricing when animals are marketed continues to be limited. To remain competitive, producers will be pressed to increase profits by maximizing production while minimizing the cost of that production. Use of sexed semen could be another tool producers could use to increase consistency in their herds, thereby capturing much needed additional value from their animals. In addition, a consistent herd could reduce labor costs to producers by allowing for the consolidation of management practices, such as gender specific implants and vaccination protocols to the majority of animals leaving only a few animals to receive an alternative scheme. When semen sexing is used in combination with a limited breeding season, producers could potentially maximize production while making better use of time and labor.

In addition to the management advantages that could be realized by using sex-sorted semen, there could be some secondary advantages when animals are marketed. Cow-calf producers would have the option to market not only a consistent calf crop for age and background, but also a crop that requires little or no additional sorting based on sex when it reaches the next stage of production. The ability to predetermine the sex of offspring could also add to the feasibility of forage based finishing programs, which would prefer females that would finish faster on forage than steers.

While sex sorted semen would have numerous applications in animal husbandry, it has direct application to human reproductions. Throughout history and cultures humans have sought control over their family, be it cultures where one gender is considered more prestigious than the other for family honor or the inheritance of property or as in the modern US where a balance between sons and daughters is often seen as ideal [3]. If science can accurately and consistently predetermine the gender of children before they are even conceived, the number of unwanted children worldwide would be reduced; leading, some have theorized, to a reduction in the world's population [3]. It is speculated that preconception gender selection would reduce the incidence of abortion and infanticide around the world [3]. However, it has been suggested that such technology would lead to a preponderance of male children due to cultural preferences throughout the world population, but this is unlikely to be a prolonged problem.

Additionally, semen sexing can lead to a reduction in the number of children born with sex-linked recessive disorders [4-5]. These disorders, which range from hemophilia to numerous mental retardation syndromes, are generally carried on the X-chromosome [4]. Male children are more at risk for suffering from sex-linked disorders than are females, because females have to inherit a copy of the defective chromosome from both parents [4]. For this reason, families with known sex-linked genetic diseases prefer to have only female children [4].

Over the years, a great deal of research has been conducted to find an effective method to predetermine the sex of offspring before conception [4]. In addition to trying to select for X- or Y-chromosome bearing spermatozoa, some techniques have focused on the nutritional status of the mother while proposing certain mineral levels in the diet have an influence on the gender of the offspring [6]. Still other studies have focused on the timing of insemination in relation to ovulation and its effects on sex outcome [6]. However, almost all existing techniques have had only limited clinical or statistical success in controlling the sex of offspring [4, 6-10]. Thus, the present inventors recognized a need for a new methodology for inexpensive semen selection, herein referred to as the Texas Tech University Semen Separation Chamber (TTU-SSC, or SSC).

In certain embodiments, the present invention may be based upon these principals: 1) sex selection can be based upon pH, 2) differences in pH will cause a repeatable pattern of cell movement, and 3) by simultaneously presenting semen cells with a choice of pH environments, each cell will select and migrate into the pH best suited for its physiology based upon simple chemical attraction. In certain embodiments, a standard commercially available four position culture plate may be used. The partitions at the center of the plate were mechanically removed and a cell strainer basket was positioned to create five separate chambers separated by the mesh of the cell strainer (FIG. 1). The openings in the cell strainer (40 or 70 μm) were large enough to allow cell movement, but small enough to prevent mass flow of fluids between chambers. FIG. 1 shows a top view and a cross-sectional side view of a container 10 that includes a main chamber 12, and sub-chambers 14, 16, 18 and 20. The main chamber 12, and sub-chambers 14, 16, 18 and 20 are separated by a biocompatible mesh 22. The main chamber 12 and sub-chambers 14, 16, 18 and 20 have a fluid therein into which the sperm are added. Each of the main chamber 12 and sub-chambers 14, 16, 18 and 20 are provided with one or one pHs as disclosed hereinbelow.

In this embodiment, typically each chamber is filled with 9 mL of media (originally a Lactated Ringer's solution, later a modified Lactated Ringer's solution was used with a non-animal protein source) with an adjusted pH. The static charge of the mesh prevented flow of solutions between chambers. The pH of each chamber seen in FIG. 1 was as follows: A—5.0, B—7.0, C—7.8, and D—9.0. The center well of the chamber (E) was filled with a semen sample prepared in the Ringer's solution at physiological pH. The pH of this solution was adjusted to 7.4 prior to the introduction of the semen sample. Once the plate was loaded with solutions it was placed in a 37° C. incubator with room air and the semen sample was allowed to migrate for varying time periods. Because of the chamber's design, sperm cells could freely move between the center well and any of the four pH solutions. While mass flow of the solutions was prevented by the mesh, finger projections of the different pH solutions could be visualized in the center chamber. These finger projections of varying pH in the center well serve as pathways to attract specific sperm populations to specific pH environments.

It is essential for all the parts of the SSC be biocompatible and nontoxic to the sperm cells. To demonstrate this, several commercially available adhesives labeled as nontoxic were used to construct SSC; they included: QuickTite Superglue, Power Poxy Super Glue Gel, orthopedic bone cement, DenTemp OS (a temporary dental filling replacement), and Liquid Stitch (a sewing adhesive). Different versions of SSC were used with each of the adhesives by first filling the plate with 10 mL per section of Lactated Ringer's. Next, the pH of the Lactated Ringer's was adjusted to 5.0, 7.0, 7.8 and 9.0 with hydrochloric acid or ammonium hydroxide before being added to the plate randomly. Boar semen was added to the center basket and the plates were allowed to incubate for 3 hours before motility and concentration readings were taken.

Figure 2:
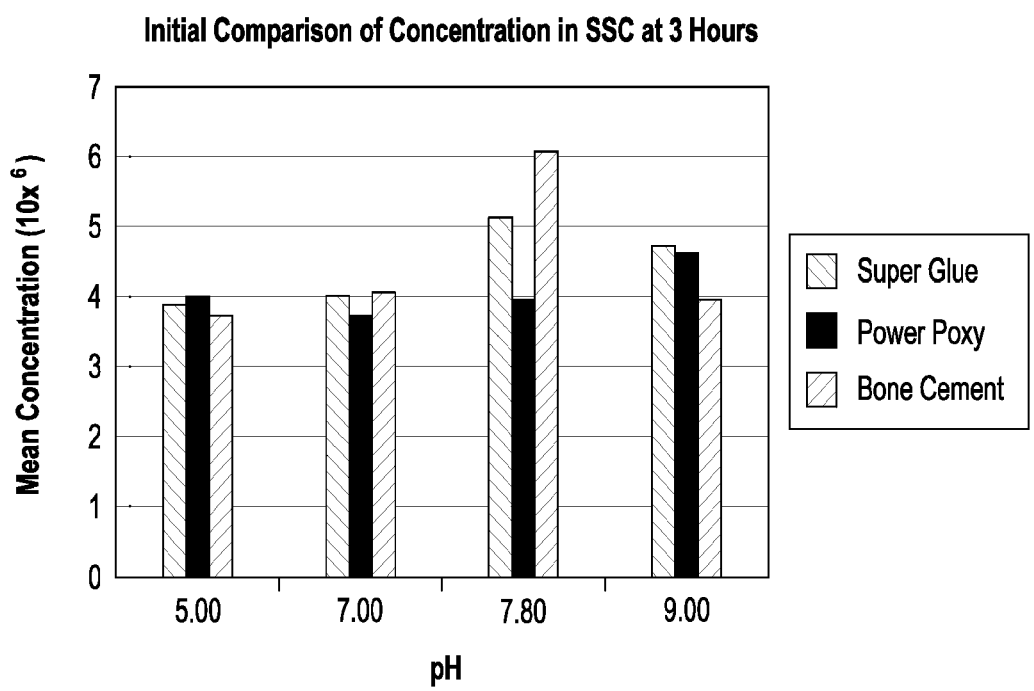
FIG. 2 is a comparison chart of the effects of the various pH environments of the Texas Tech University Semen Separator Chamber (SSC) on sperm concentration and the influence of the various glues used for construction.
Figure 3:
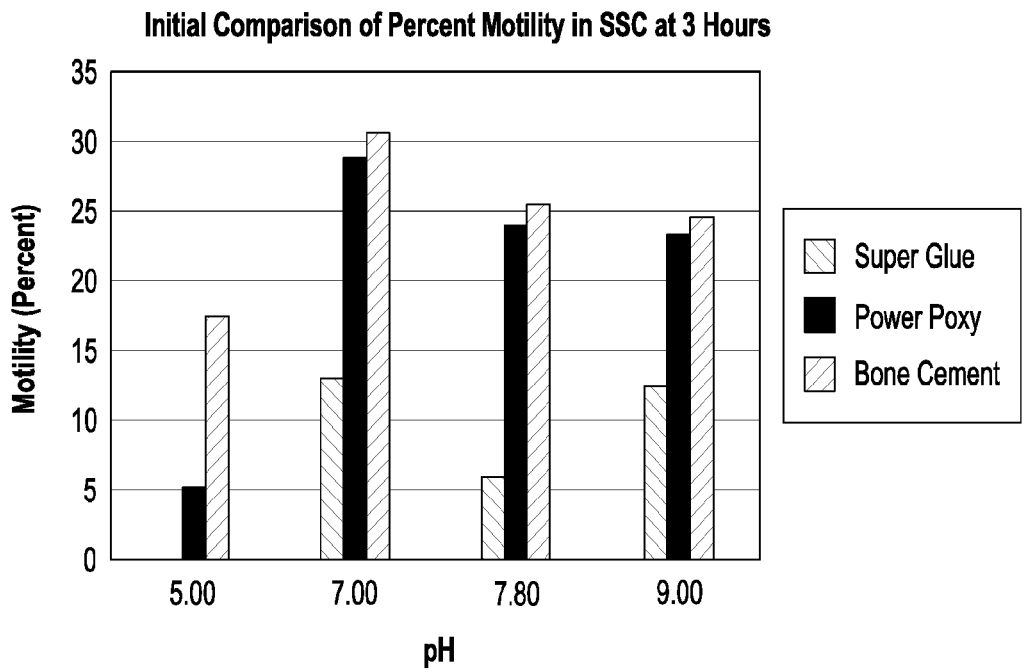
FIG. 3 is a comparison chart of the effects of the various pH environments of the Texas Tech University Semen Separator Chamber (SSC) on sperm motility and the influence of the various glues used for construction.

As shown in FIG. 2, the adhesive have little effect on the migration pattern of sperm cells as the concentration of cells in each chamber was similar (P=0.703; FIG. 2). Further, pH have little effect on the migration pattern when looking at concentration (P=0.283). However, the number of cells migrating into each chamber was significantly lower than expected. There was a significant decrease in motility within the first three hours which appeared to be dependent on both the adhesive used to construct the plate (P<0.002; FIG. 3) and the pH within the specific chambers (P<0.024).

To further demonstrated the biocompatibility of the SSC, different versions of the device were constructed by creating several divided petri dishes with each well trying to simulate a process or component of the proposed device. At least one well was left as the plate had been manufactured which served as a control for the other components. To simulate the cutting action required to fit the cell strainer into the petri dish the bottom of one well was abraded by the cutting wheel of the Dremel Rotary tool. In addition to cutting, the bottom of one well was melted with hot metal.

Several small dots of each adhesive were placed on the bottom and allowed to cure before being exposed to boar semen extended with either Lactated Ringer's or Lactated Ringer's supplemented with 10% Newborn Calf Serum Albumin (BSA). The final construction component used was the basket, which was affixed to the bottom of one well by heating the plastic frame and pushing it onto the bottom of a petri dish. All wells were filled with boar semen extended with Lactated Ringer's solution. In addition, blank wells were filled with boar semen extended with Modified Eagles Media or Media 199 to eliminate bias based on the extender and to determine if any of these media preparations would be useful. A boar semen sample was added to each section of the plate and motility and concentration readings were taken at 3, 6, 12, 18, 24 and 30 hours.

Figure 4:
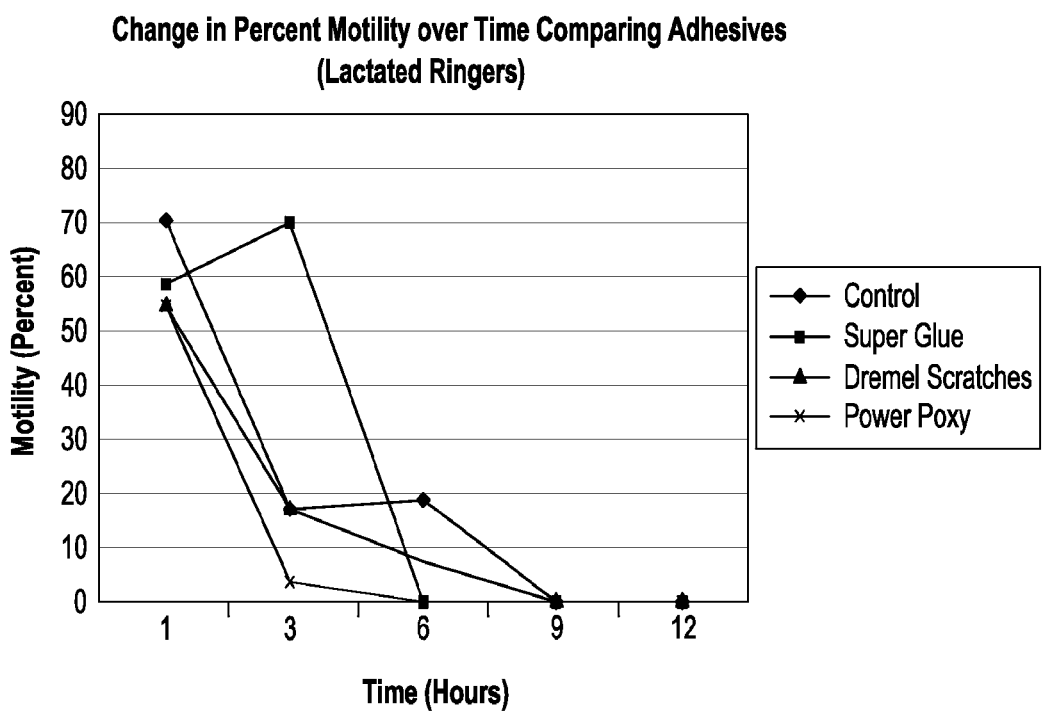
FIG. 4 is a chart comparing the effect of various adhesives on sperm motility over time cultured in a Lactated Ringer's salt solution as a media.
Figure 5:
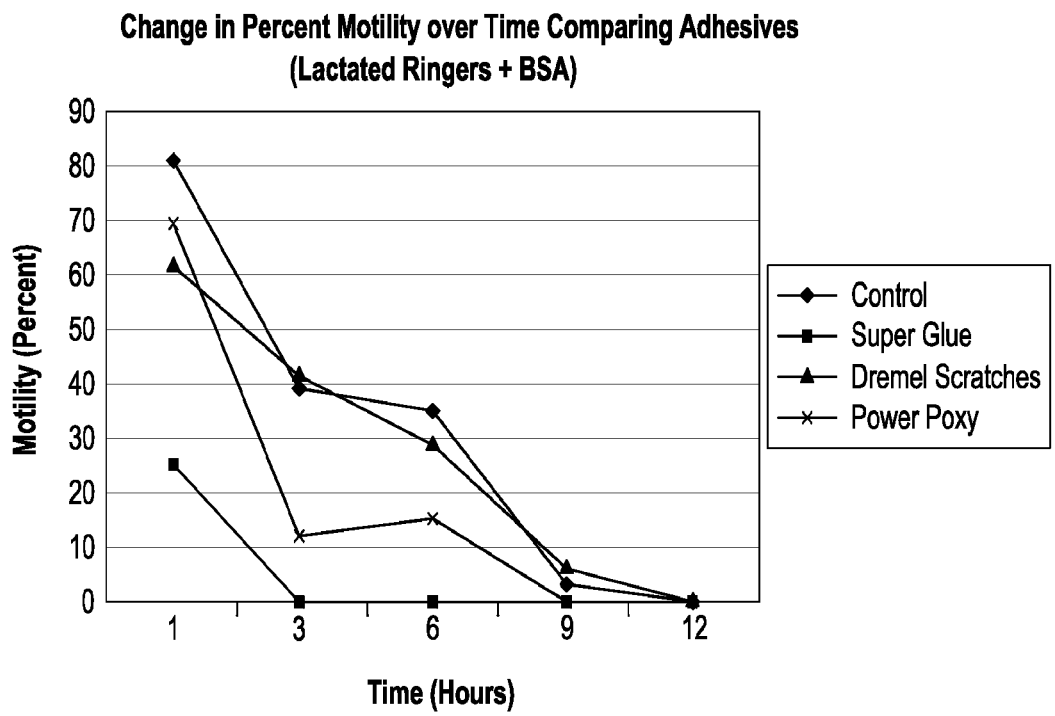
FIG. 5 is a chart comparing the effect of various adhesives and a simple plastic cutting process on sperm motility over time cultured in a Lactated Ringer's salt solution supplemented with 10% Bovine Serum Albumin as a media.

As seen in FIGS. 4 and 5, motility decreased over time regardless of treatments (P<0.001). However, in some embodiments quicktite superglue and power poxy, were toxic to sperm cells with all cells reaching zero motility by nine hours, whereas the control samples remained 2% motile (P<0.001). Sperm motility was also affected significantly by the media used with the Lactated Ringers containing BSA maintaining significantly higher motility than Lactated Ringers without (P<0.001), indicating sperm survived better in the presence of a protein enriched media. The single treatment with results similar to the control was in wells etched with the Dremal tool, where motilities were similar to the control over the 12 hour period, indicating this method was acceptable for modification of the plates.

Figure 6:
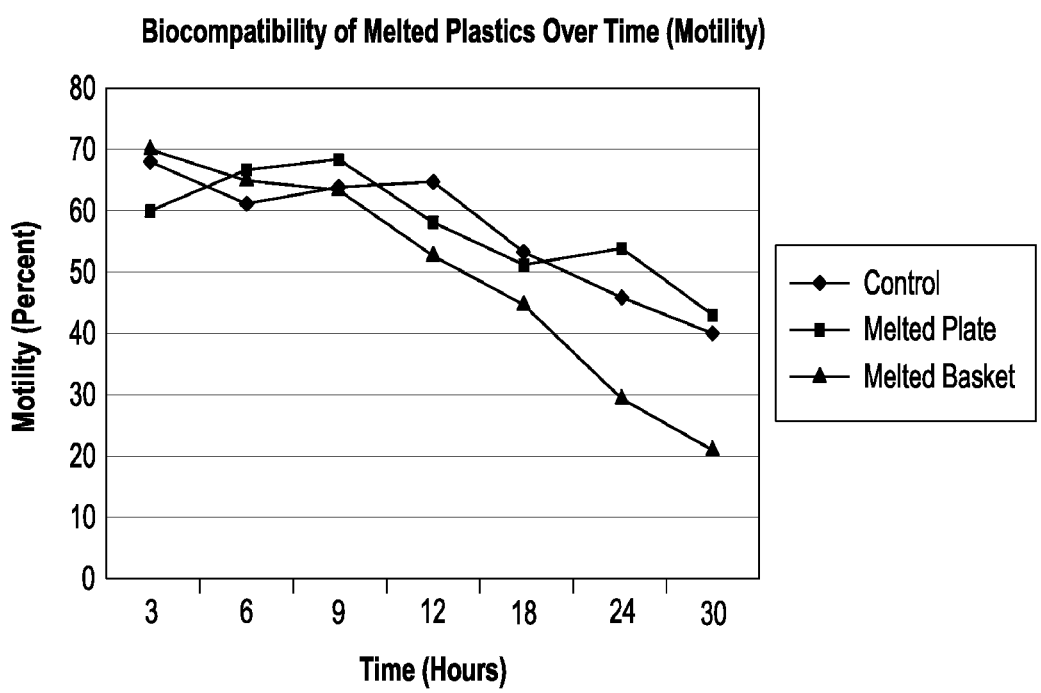
FIG. 6 is a chart demonstrating that melting combined with the plastics cutting process has little effect on sperm motility.

Further, different heat welding methods were used as means of attaching the baskets to the Petri dish. In certain embodiments, Petri dish and the cell strainer basket may be melted and exposed individually to extended boar semen. As demonstrated, sperm motility decreased with time (P>0.001; FIG. 6). However, the decrease is motility was similar to that of cells in the control (P=0.172) showing that "welding" the plastics together did not release toxins into the system and would be a biocompatible method for creating a watertight seal between the dish and cell strainer to create the SSC.

Also, different meshes were used in different versions of SSC. Here, results of migration patterns of sperm cells out of the 40 and 70 micron mesh baskets were statistically similar (P=0.727). The present inventors recognized the smaller mesh baskets formed a better electrostatic barrier between chambers (i.e. prevention of mass flow of water during filling).

Furthermore, different media were used as extenders in the plates. FIG. 4 and FIG. 5 demonstrates that Ringer's lactate with 10% BSA was superior to Ringer's lactate alone in maintaining cell motility (P<0.001; FIGS. 4 and 5). In addition, Media 199, and Modified Eagles Media may be used in other embodiments in an attempt to improve motility over time.

Figure 7:
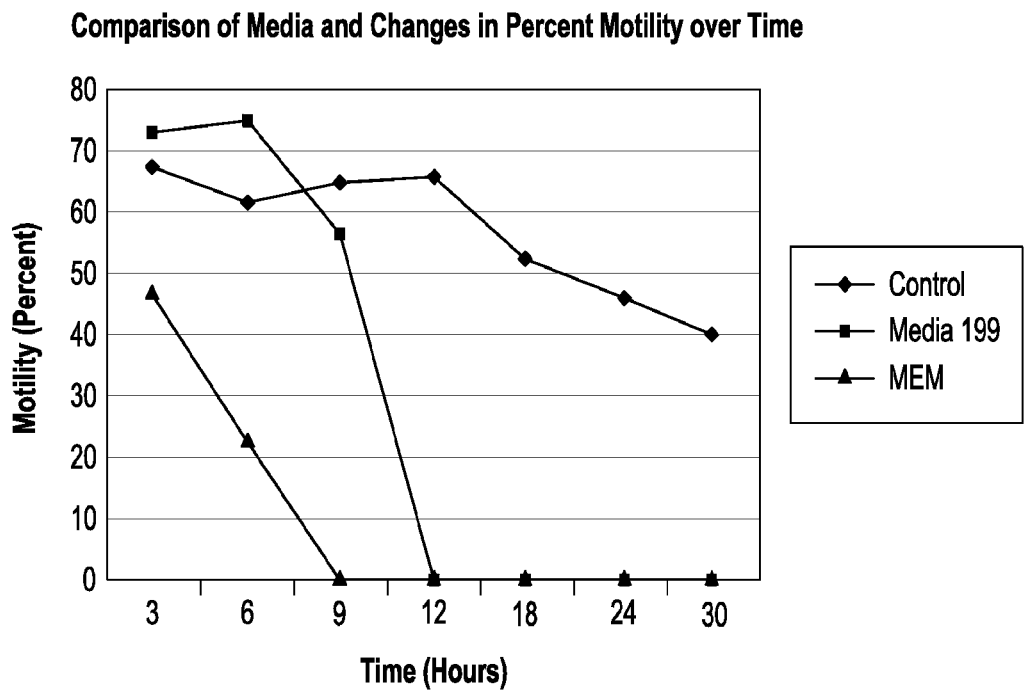
FIG. 7 is a comparison chart of three specific media as components for the SSC; demonstrating the superiority of the control media on support sperm motility over time.

FIG. 7 demonstrates motility decreased over time (P<0.001; FIG. 7) regardless of different media used. However there were differences in motility due to media affects alone (P<0.001) and in interaction with time (P<0.001). Cells cultured in Media 199 or Modified Eagles Media had reached 0% motility by 12 hours of culture, whereas cells in the modified Ringer's Lactate solution maintained 40% motility to at least 30 hours (P<0.001). This demonstrates that the modified Ringer's Lactate solution was the superior media.

pH Behavior. In certain embodiments, the present invention provides the sperm cells with different pH adjusted mediums simultaneously. This allows the sperm cells to migrate directly from the original media into (and potential out of) any of the four environments and toward the preferred pH based on the sex of the sperm.

To demonstrate that the separation plate maintains pH in discretely separate chambers while allowing the sperm cells to migrate freely within the separator, three different studies were constructed. In brief, the first study shows the behavior of four pH adjusted media solutions in a standard four section Petri dish. The second study shows the behavior of the same solutions in the current device. In the last study, colored dyes were used to visualize media movement within the current device.

First, Lactated Ringer's was prepared as described earlier, pH adjusted to 5.0, 7.0, 7.8, and 9.5 plus or minus 0.10. Ten mL of the adjusted media were placed in an uncut petri dish used for the construction of the semen separator to maintain approximately the same surface area as the device when constructed. For each study, 3 plates were used and the different media were placed in a different position and order for each group of 3 plates, this was done to show if position or order had an effect on the maintenance of pH. Measurements were taken, recording the pH of each well of all 3 plates, every 15 minutes for the first 2 hours, then hourly to 6 hours and again at 24 hours, using a Thermo Orion 8135 surface pH probe and an Accumet Research AR25 Dual Channel pH/Ion meter.

Figure 8:
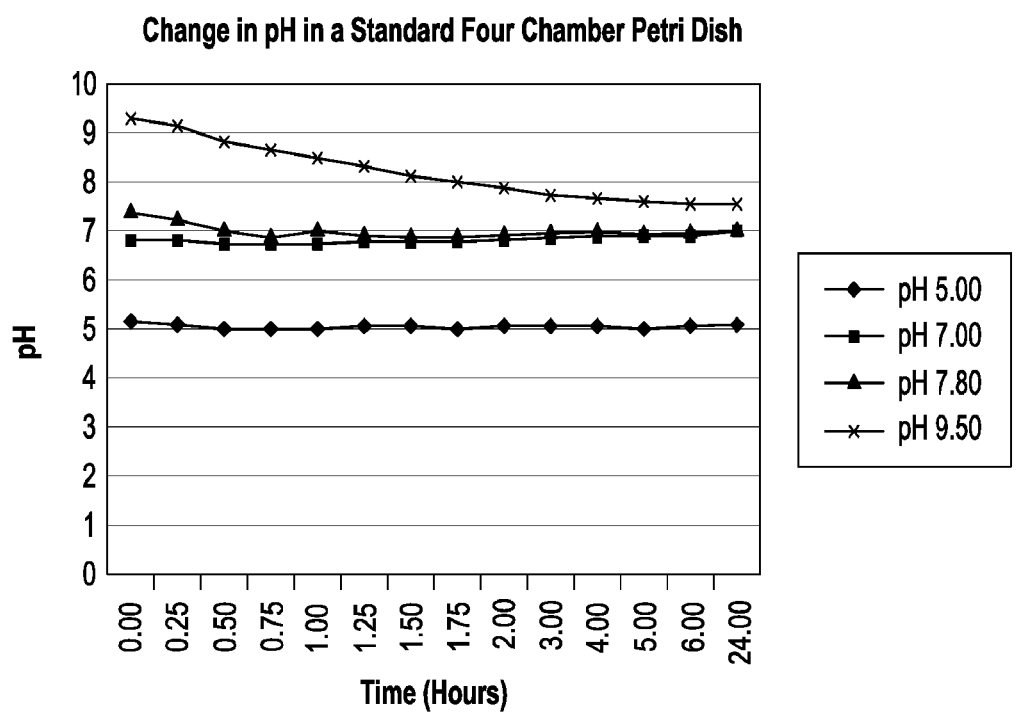
FIG. 8 is a chart demonstrating the stability of pH adjusted modified Lactated Ringer's solution over time.

In the first study, regardless of placement order or position in the plain, four-section Petri dish, there were pH fluctuations. The degree of the fluctuation was dependent on starting pH (P<0.001). The most notable fluctuation was the pH drop observed in the 9.5 well, which dropped from very basic to within physiological range by 2 hours then stabilized (FIG. 8). The two mediums set to within physiological range, 7.0 and 7.8 encountered a slight drop with 7.0 initially dropping into the high 6 range and only returning to pH 7.0 toward the end. The drop of 7.8 did not reach the same acidic level as 7.0 but it also dropped into the high 6 range momentarily before again rising to around neutral. Only 5.0 remained approximately constant through 24 hours.

To demonstrate how pH would behave in the SSC, the same procedure was followed in the second study; however, 9 mL of pH adjusted media were used for each of the four wells to allow room for the addition of the basket. A different filling pattern was used with each group of 3 plates, which was comparable to the technique used to fill the plates to facilitate comparison between plates with and without the basket. The center well of the device was filled with 5 mL of Lactated Ringer's adjusted to 7.4 to mimic physiological pH. Care was taken to ensure that the center well did not flood with the media from the outer wells before media was added to the center. Measurements were taken as previously described every 15 minutes for the first 2 hours, then hourly to 6 hours and finally at 24 hours.

Figure 9:
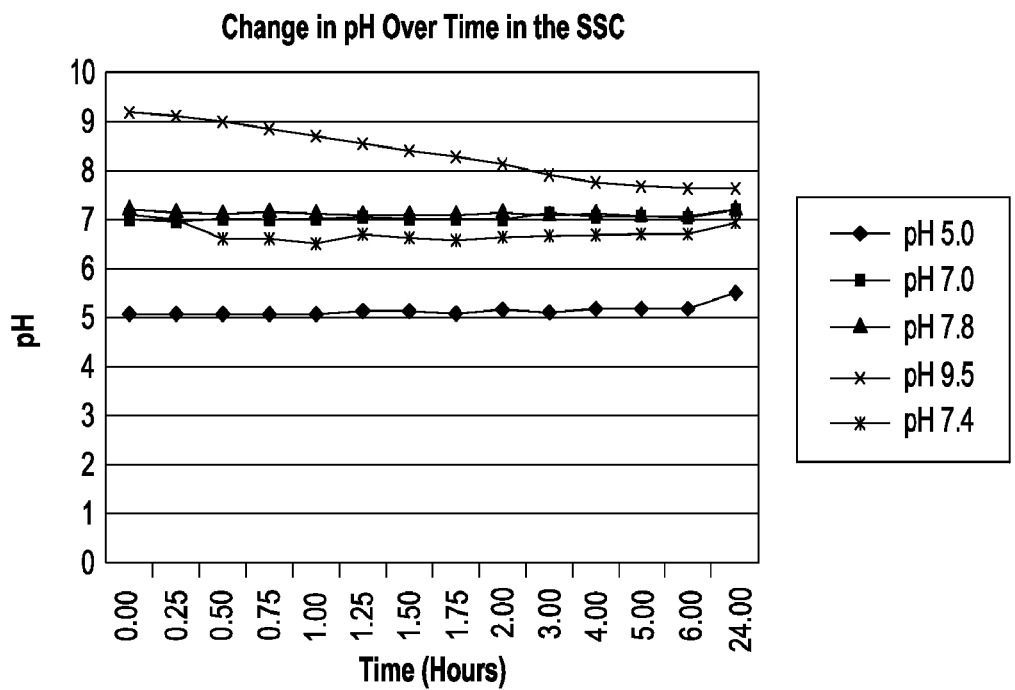
FIG. 9 is a chart showing the behavior of pH adjusted modified Lactated Ringer's solution in the Texas Tech University Semen Separator Chamber over time.

In the second study, it showed that regardless of placement order or position in the SSC there are some minimal pH fluctuations consistent with those observed in the plain Petri dish. However, the center well experienced a significant shift going from a set pH of 7.4 to approximately 6.4 within the first hour. (P<0.001; FIG. 9).

To assist in visualizing movement of solutions between chambers, the third study was prepared as described above, and with four pH adjusted Modified Lactated Ringer's with 10% Non-Animal Protein Source (NPS) media, 5.0, 7.0, 7.8, and 9.5. However, each media was dyed with 3 drops of food grade coloring pH 5.0 was dyed yellow, 7.0 was dyed red, 7.8 was dyed green and 9.5 was dyed blue. The center well was filled with a clear solution that was pH 7.4. The plate was allowed to incubate at room temperature on a lab bench for 24 hours and photographs were taken at 1, 3, 6, and 24 hours to qualify diffusion of fluids across the center well.

Figure 10:
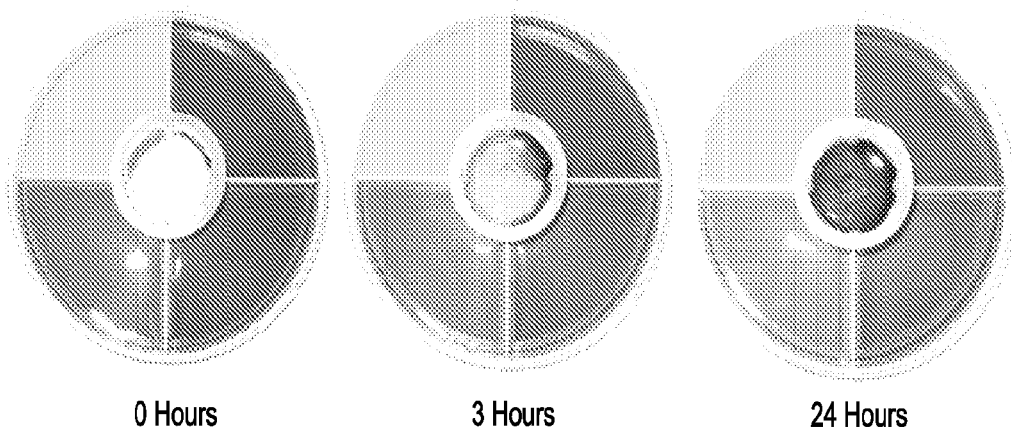
FIG. 10 is a visualization chart of ion exchange over time between chambers of the Texas Tech University Semen Selection Chamber; yellow=pH 5.0, red=pH 7.0, green=pH 7.8 and blue=pH 9.5.

To visualize these findings and to demonstrate the radical change in the pH of the center well was caused by an exchange of ions between the pH 5.0 well and the center, food grade dyes were added to each of the four other wells and their movement tracked over time. As illustrated in FIG. 10, each dye began to penetrate the center well as early as one hour. This minor penetration created finger-like projections, similar to cervical mucus, to attract sperm cells to a particular outer well. Further, while the center chamber involves a mixing of solutions, there appeared to be no mixing of solutions between the outer chambers.

pH Migration. In order to demonstrate that SSC allows separation in a pattern based on DNA content, bull and boar semen were used with the present invention.

Boar Semen. Nine semen samples were acquired from eight breeding boars at the Texas Tech University Swine Unit in New Deal, Tex. The semen samples were extended 2:1 with a commercial semen extender designed for boar semen and then transported to the Texas Tech University Health Sciences Center Obstetrics and Gynecology Laboratory where the samples were further processed. The semen samples were divided into 2 parts and centrifuged (300 rpms) for 10 mins, the supernatant was poured off. One pellet was suspended with a calcium carbonate based Lactated Ringer's with 10% Newborn Calf Albumin the second pellet was suspended with calcium carbonate based Lactated Ringer's with 10% soy protein [11]. The soy protein was prepared by combining 1.5 g of soy flour with 100 mL of prepared calcium carbonate based Lactated Ringer's and allowed to warm in a 37° C. waterbath for 30 minutes. Next, the solution was given time to cool and then filtered twice through several layers of non-sterile cotton gauze to remove excess particulate matter, then through a 0.45 μm Nalgene filter and then finally a 0.22 μm Nalgene filter. The soy solution was refrigerated and combined with the prepared Lactated Ringer's media at a rate of 10%. The two pellets were combined and extended with sufficient Lactated Ringer's and Soy extender to equal 20 mL of semen.

The SSCs were constructed using either a 70 μm or 40 μm nylon cell strainer baskets. The cell strainer basket was trimmed, the bottom of the basket removed and fitted into a four section compartmentalized petri dish that had the center cut away as previously described. The basket was fused to the petri dish using a 40 watt soldering iron model SL-5-40, set to a temperature hot enough to melt the two plastics. Care was taken not to melt through the petri dish or the mesh, but to assure a water-tight seal at all seams. Once manufacturing was completed, the plates were filled with 9 mL of deionized water to check for leaks and then rinsed with deionized water and allowed to dry upside down, at least overnight at room temperature.

To prepare the device for use, it was labeled and placed in a 37° C. incubator for a minimum of 30 minutes. Each chamber of the device was then filled with 9 mL of prewarmed pH adjusted extender with 5.0 being placed in the upper left hand quadrant, then 7.0 in the upper right hand quadrant, 7.8 in the lower left hand quadrant, and finally 9.5 in the lower right hand quadrant. Care was taken so that extender did not flood the center mesh well. Initially, the center well was filled with 5 mL of extended boar semen. Subsequently, 3 mL of boar semen was found to be adequate to fill the center well. As there were concerns on the ability of cells to migrate through smaller mesh baskets, each boar sample was processed through two plates utilizing baskets of 70 μm mesh and two utilizing the 40 μm mesh screen. Once the plates were prepared, an initial concentration and motility was taken on the sample in the center well, and the plates placed in a 37° C. incubator for 24 hrs. The concentration of sperm cells was determined in each well of the SSC at times 1, 6, 12, 18 and 24 hours, motility readings were determined at 1, 3, 6, 9, 12, 15, 18 and 24 hours in each of the four pH modified chambers. Finally, at each time point, samples were taken and fixed with an equal volume of 3% formalin for potential use in fluorescent in situ hybridization to determine chromosomal content.

While SSC needs a protein source to operate, agglutination were occasionally observed, and can potentially prevent cell migration through the basket mesh. Since Lactated Ringers with 10% of soy based protein caused less agglutination of sperm cells than did a Lactated Ringers with 10% BSA soy protein was substituted as a preferred embodiment.

Figure 11:
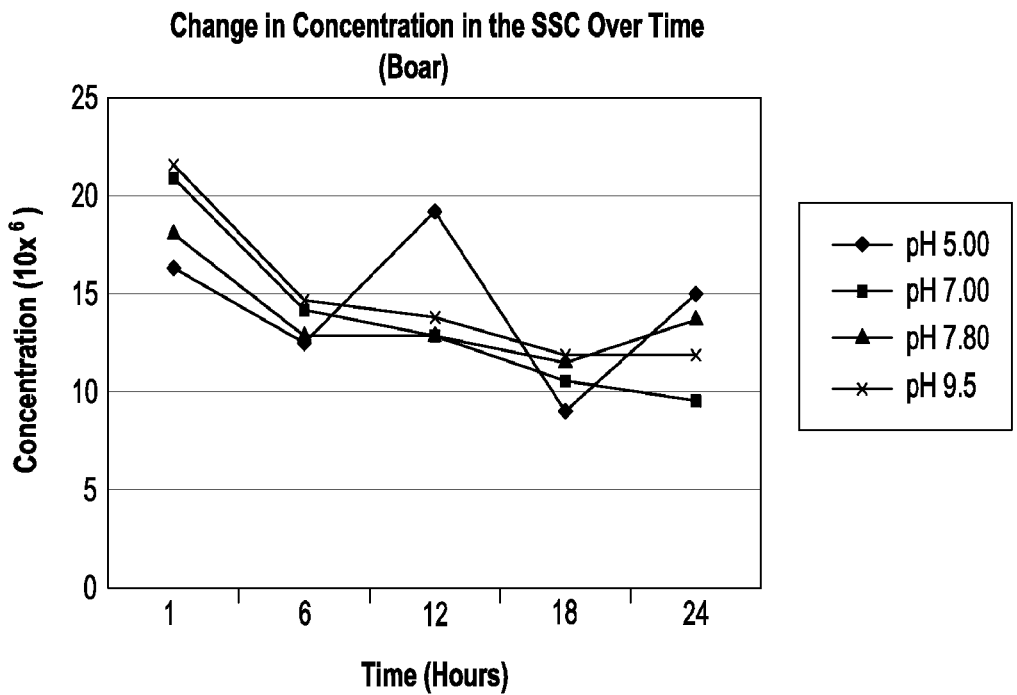
FIG. 11 is a diagram showing changes in total sperm concentration for boar sperm over 24 hours in each well of the Texas Tech University Semen Separator Chamber (SSC).
Figure 12:
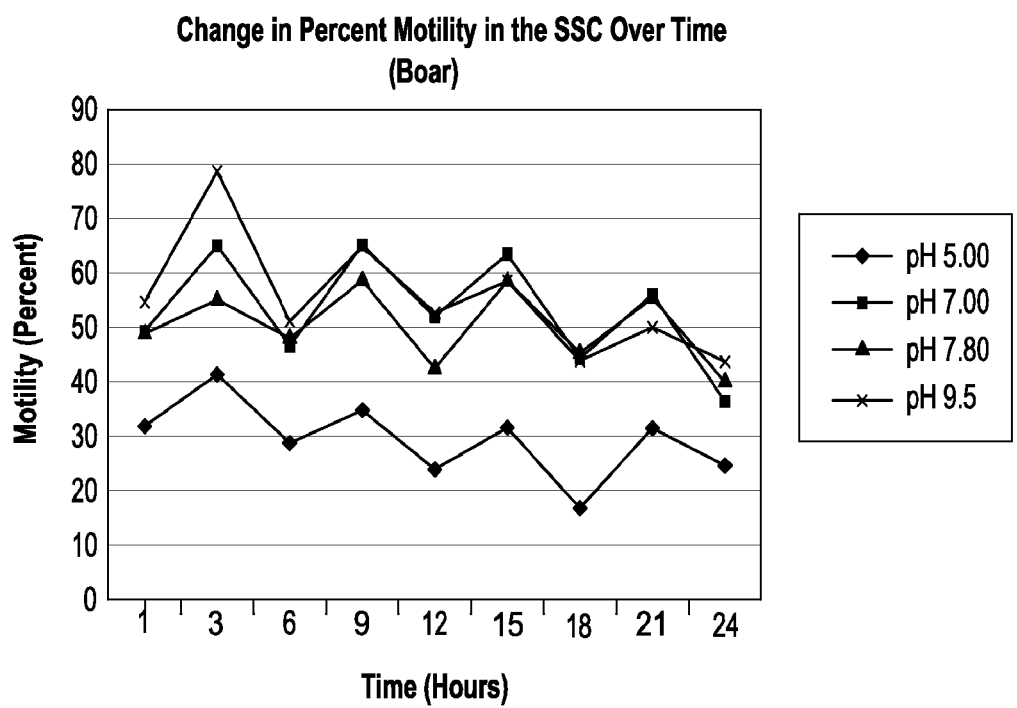
FIG. 12 is a chart which describes sperm motility in the Texas Tech University Semen Separator Chamber (SSC), demonstrating the effects of pH and time.

Sperm concentration was used as an indicator of sperm movement within the SSC with readings being taken at fixed points (1, 6, 12, 18 and 24 hours). As demonstrated, there were significant shifts in concentration over time ($P<0.001$; FIG. 11) with the most significant change coming from hour 0 to hour 1 where concentration in the four outer chambers went from zero to approximately 20 million cells per mL for all treatments. Further, there were no significant differences in concentration ($P=0.848$) showing no difference in total (both motile and non-motile) cell migration patterns based on the pH. However, while the total number of cells did not differ, there were significant differences in motility across the four pH adjusted media ($P<0.001$) and decreased over time ($P<0.001$). Motility was initially highest in the media adjusted to a pH of 9.5 (FIG. 12). This trend continued through the six hour time point, but by 9 hours the motility of this group was similar to that of the media initially adjusted to 7.0 and 7.8 and remained similar through the end of. Because of the extreme acid conditions which remained low for an extended period of time (FIG. 9), motility was initially lowest in the media adjusted to pH 5.0 and remained lower throughout. While motility decreased over time, there was no interaction with the effects of pH ($P=0.615$) indicating the effects of pH in the SSC could be used to manipulate cell migration.

Bull Semen. Ejaculates were obtained from 14 Brangus and Angus bulls ranging in age from 16-24 months of age courtesy of veterinary clinics and private owners in Throckmorton, Tex., Dimmit, Tex., Abernathy, Tex. and Lamesa, Tex. as part of regular breeding soundness examinations. The ejaculates were collected and extended 2:1 in commercial extender for transport back to the Texas Tech University Health Sciences Center Obstetrics and Gynecology Laboratory where the samples were further processed. The semen samples were centrifuged (300 rpms) for 10 minutes and the supernatant was poured off. The pellet was suspended in a calcium carbonate based Lactated Ringer's media supplemented with 10% of a Non-Animal Based Protein Source (NPS). The NPS media was prepared as described above for the soy protein media used.

The SSC devices were constructed prior to obtaining the semen sample. As previously demonstrated, the boar semen shows little difference in cellular movement between SSC with 70 versus 40 mesh baskets. The SSC were constructed and prepared for used following the procedure previously described. Each chamber of the device was then filled with 9 mL of pH adjusted NPS extender, with 5.0 being placed in the upper left hand quadrant, then 7.0 in the upper right hand quadrant, 7.8 in the lower left hand quadrant, and finally 9.5 in the lower right hand quadrant. Care was taken so that extender did not flood the center mesh well. Finally the center well was filled with 3 mL of extended bull semen. The bull samples were incubated for 6 hours with motility and concentration readings being taken at 3 and 6 hours. At 6 hours the media from each of the four outer chambers and the center mesh well were collected and centrifuged to form a pellet of migrated sperm. The pellet was then suspended in 1 mL of NPS Lactated Ringer's Media; this volume was then divided in half with 0.5 mL being frozen in liquid nitrogen and 0.5 mL being immediately processed for florescence in situ hybridization analysis.

Figure 13:
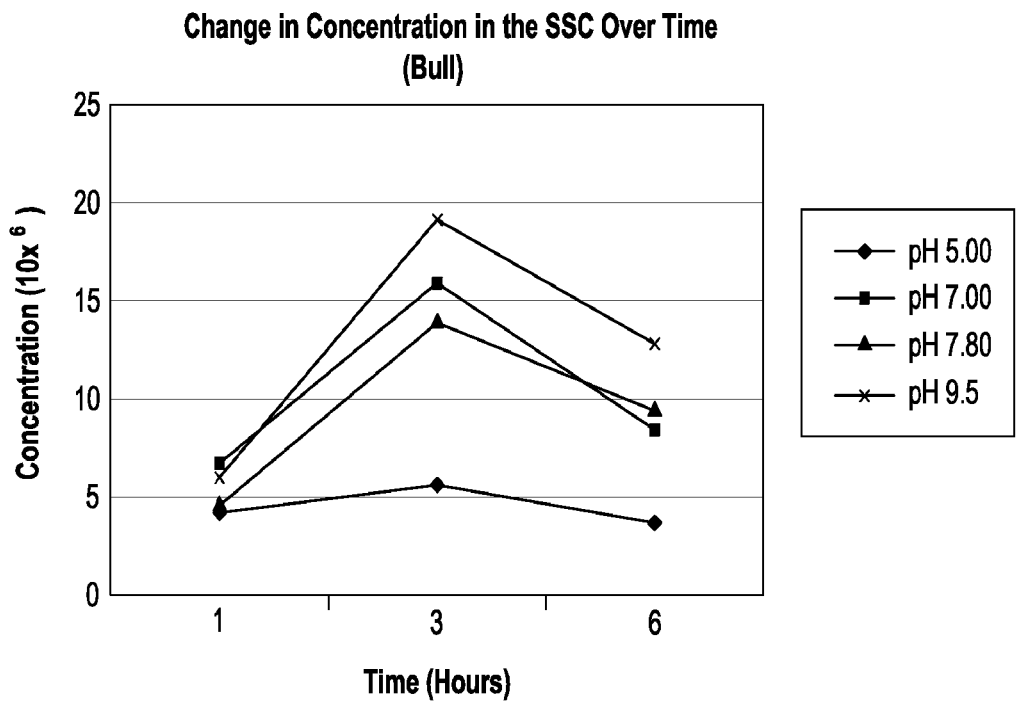
FIG. 13 is a chart showing changes in total sperm concentration for bull sperm over 6 hours in each well of the Texas Tech University Semen Separator Chamber.
Figure 14:
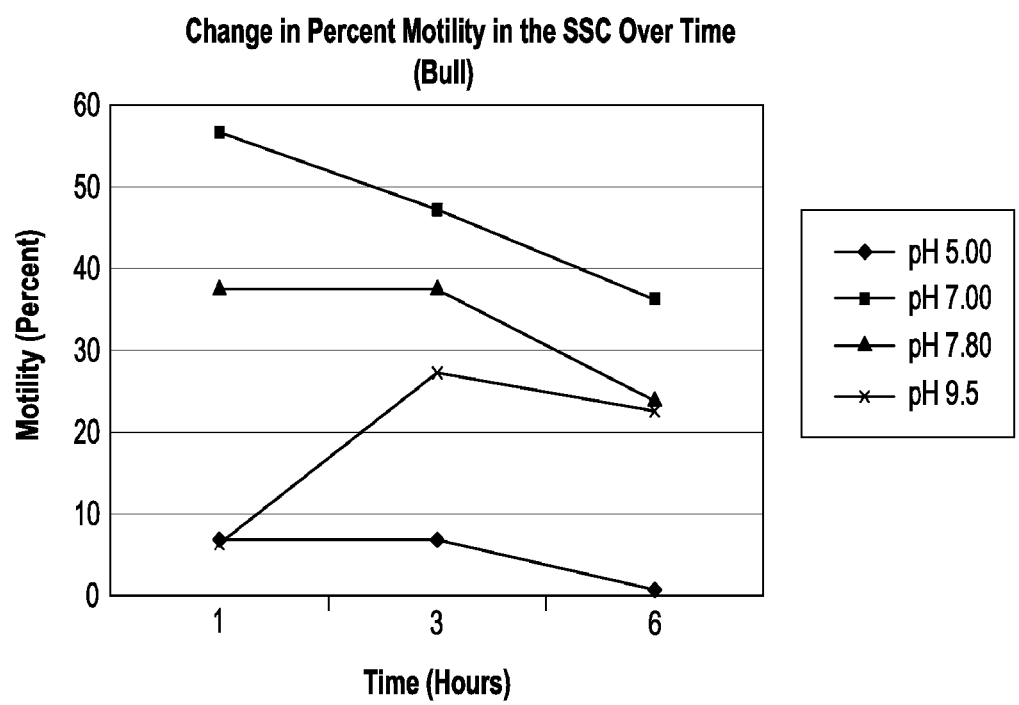
FIG. 14 is a diagram describing changes in bull sperm motility over 6 hours in each well of the Texas Tech University Semen Separator Chamber (SSC).
Figure 15:
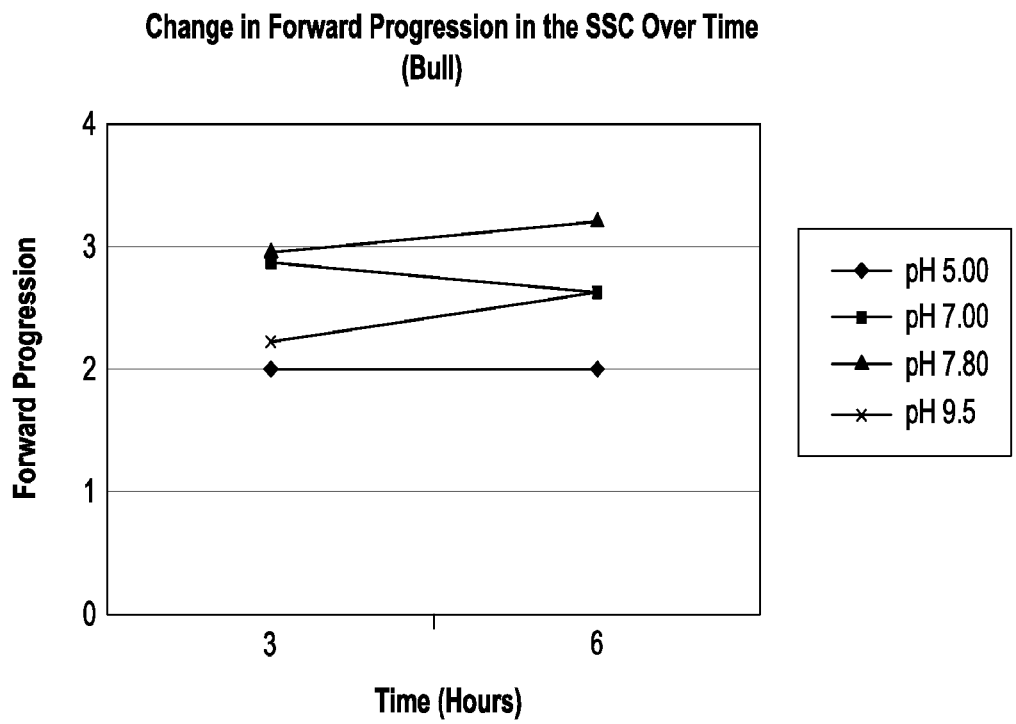
FIG. 15 is a chart showing changes in cell forward progression for bull sperm over 6 hours in each well of the Texas Tech University Semen Separator Chamber.

In order to have cells available for Fluorescent in situ hybridization (FISH) analysis and pH migration demonstration were needed using the bull semen model. As shown previously, concentration increased in each of the outer wells over time ($P<0.018$; FIG. 13). The shift was highest between 0 and 3 hrs. However, contrary to results observed in the boar, there was a trend ($P=0.086$) toward higher total cell concentrations with increasing pH. As determined in the boar semen, motility was significantly affected by both the pH of the media as well as time ($P<0.001$ and $P<0.023$ respectively; FIG. 14).

Fluorescent In Situ Hybridization. Fluorescent in situ hybridization (FISH) is an analysis technique by which specific chromosomes or chromosome regions can be visualized and studied using fluorescent microscopy. It is widely used in clinical medicine and research applications for both humans and animals, often for the detection of genetic markers in disease conditions and for the sexing of embryos for assisted reproductive techniques [12-14].

The bull samples were analyzed using chromosome paint for the detection of bovine X- and Y-chromosomes and a sexing protocol developed specifically for sperm. A typical FISH protocol for the detection of the X- and Y-chromosome in bovine sperm can be performed as a two or three day protocol and has several major steps; Sperm Washing, Decondensation of Sperm, Pepsin Treatment, Slide Denaturation, Probe Preparation and Denaturation, Hybridization, Washing, Detection and Mounting. In certain embodiments, prior to beginning the first day solutions were prepared and sterilized using manufacturer suggested techniques. In brief, the 20 X sodium citrate (20×SSC) solution was prepared by combining 87.6 g of sodium chloride and 44.1 g of sodium citrate with enough HPLC grade water to equal 500 mL. One hundred mL of prepared 20×SSC solution is then added to 400 mL of HPLC water to make 4× sodium citrate (4×SSC). For 2× sodium citrate (2×SSC), 50 mL of 20×SSC solution is added to 450 mL of HPLC water and finally to create 1× sodium citrate (1×SSC) solution 25 mL of 20×SSC solution is added to 475 mL of HPLC water. All SSC solutions are then autoclaved for sterilization. Solution A is made from 0.605 g of Tris combined with 4.5 g of sodium chloride and enough HPLC water to bring the total volume to 500 mL and then autoclaved. Solution B is made by combining 0.38 g of DTT with 10 mL of solution A and then divided into 0.5 mL aliquots and frozen. Solution C is made from 5.7 g of di sodium tetraborate and 3 g of SDS combined with enough HPLC water to equal 300 mL. This solution is also divided into 0.5 mL aliquots and frozen. To create the pepsin solution used in the pepsin wash step, a 10 mM hydrochloric acid solution is made by mixing 10 mL of 1 M hydrochloric acid with 90 mL of HPLC water and autoclaved. Next a 1% pepsin solution is made by adding 1 g of pepsin powder with 100 mL of HPLC water. This solution is divided into 1 ml aliquots and frozen. For the pepsin wash solution, combine 0.5 mL of 1% pepsin solution with 49.5 mL of 10 mM hydrochloric acid solution. Make this wash solution fresh for every run. The denaturation solution is 70 mL formamide and 30 mL 2×SSC this solution must be made fresh for every run. The stringency wash is 50 mL formamide and 50 mL of 1×SSC and this solution can be refrigerated and reused up to five times. The detergent wash solution is made from 250 µL of detergent DT provided by the manufacturer (or tween 20) and enough 4×SSC to equal 500 mL. This solution can be halved for smaller runs and may be held for 3 days if stored at 4° C.

Step one was to wash the sperm cells. One-half milliliter of sperm suspension was added to 1 mL of a tris and sodium chloride solution (solution A) and centrifuged for 10 minutes at 2000 rpm. The supernatant was then removed and the pellet resuspended in 50 µL of the tris and sodium chloride solution (solution A). Next the sperm cells were decondensed to allow the probe to penetrate the densely packed chromatin structure found in spermatozoa. This was achieved by combining 5 µL of the sperm solution with 5 µL of diluted DTT in the tris and sodium chloride solution (solution B) and incubating this mixture for 2.5 minutes. The next step was to add 5 µL of the di-sodium tetraborate and SDS solution (solution C), incubate the sperm for an additional 10 seconds and then add 50 µL of chilled absolute ethanol to stop the reaction. A 5 µL drop of the decondensed sperm solution was placed onto an ethanol cleaned slide and the slide was allowed to dry on a slide warmer. To insure location of the sperm cells at later steps, the area of the sperm field was outlined with an etching pencil. The slides were then incubated in absolute ethanol for five minutes and dried at room temperature. The next step was to treat the slides with pepsin to digest portions of the cellular membrane by incubating them in a pepsin solution for 30 minutes at room temperature. The slides were then washed for three minutes in 2×SSC and rinsed in distilled water for six seconds followed by serial dehydration in 70% ethanol twice for two minutes each, 90% ethanol twice for two minutes each and finally five minutes in absolute ethanol. The slides were then dried at room temperature before baking them for 30 minutes at 65° C.

The next step was to denature the slides by placing them immediately from the slide warmer into a denaturation solution of 70% formamide in 2×SSC solution heated to 65° C. for one minute, followed immediately by incubation in ice cold absolute ethanol for five minutes. A serial dehydration step was then performed as described previously and the slides allowed to dry at room temperature. At this point the slides were examined under a phase contrast microscope looking for cells with swollen heads and degraded but still partially intact tails.

The chromosome probe was denatured prior to being placed on the slide by incubating it in a 65° C. waterbath for 10 minutes then plunging it into ice. The probe and sperm chromosomes were then hybridized by placing 10 µL of denatured probe onto the slide, covering it with a coverslip and sealing with rubber cement. The slides were then incubated in a dark humidified chamber at 37° C. overnight.

The first step on day two was preparation and warming of washing solutions to 45° C. The wash solutions include two coplin jars each containing at least 50 mL of stringency Solution, two coplin jars containing at least 50 mL of 1×SSC solution and three coplin jars containing at least 50 mL of detergent wash Solution with all solutions prepared as previously described. Once the solutions were prepared, the coverslips were removed from the slides by incubating them in room temperature 1×SSC for five minutes to soften the rubber cement seal, and then peeling the rubber cement from the surface. The slides were then soaked in the 1×SSC until the coverslip floated off. The slides were then washed twice for five minutes in 45° C. stringency wash solution of 50% formamide in 1×SSC, followed by washing the slide twice for five minutes at 45° C. in 1×SSC. Finally, the slides were incubated three times in 45° C. detergent wash solution by submerging the slides fully in each solution for the prescribed time and moving to the next incubation step without allowing the slides to dry out. It should be noted that for the washing procedure temperature is critical temperature should be taken inside the coplin jars and not the fluid surrounding the coplin jars in the waterbath.

The detection reagents were prepared as described in the detection protocol provided in the FITC/CY3 Detection kit. In brief, while performing the wash steps above, thaw the blocking protein provided by the manufacturer and combine 190 µL with 1060 µL of detergent solution and mix thoroughly, this is working reagent A (these volumes are for when staining 10 slides, but these volumes may be halved for five slides). For working reagent B combine 2.5 µL of detection reagent B1 provided by the manufacturer with 617.5 µL of working reagent A, this solution is incubated in the dark for five minutes and then centrifuged at 11,000 g for five minutes. Working reagent C is made by adding 5 µL of detection reagent B2 provided by the manufacturer with 615 µL of working reagent A, this solution is also to be incubated in the dark for five minutes and then centrifuged at 11,000 g for five minutes. To prepare working reagent D combine the equal volumes of working reagent B and working reagent C supernatant, being sure to provide 100 µL for each slide. After the reagents were prepared, 100 µL of the working reagent D was applied to each slide and the slide covered with parafilm. The slide was then incubated in the dark for 15-20 minutes at 37° C. After the incubation, the parafilm was removed and the slides washed three times for four minutes each in room temperature detergent wash solution.

The slides were mounted by draining them thoroughly, removing as much of the detergent wash solution without allowing the slides to dry out, then applying 30 µL of provided mounting reagent, covering with a coverslip, and sealing the edges with clear nail varnish. The slides were then either observed under fluorescent microscopy, or stored at −20° C.

Observation of the slides was performed on a Nikon Optihot Microscope equipped with epifluorescence. The scope was equipped with fluorescent cubes to detect FITC and for the counterstain DAPI. Slides were randomly examined by one or two trained observers, each observer examined 500 cells by switching between fluorescent cubes to determine if the signal was red or green. Complete fields of the slide were evaluated for both red and green signals before moving on to the next field.

Figure 16:
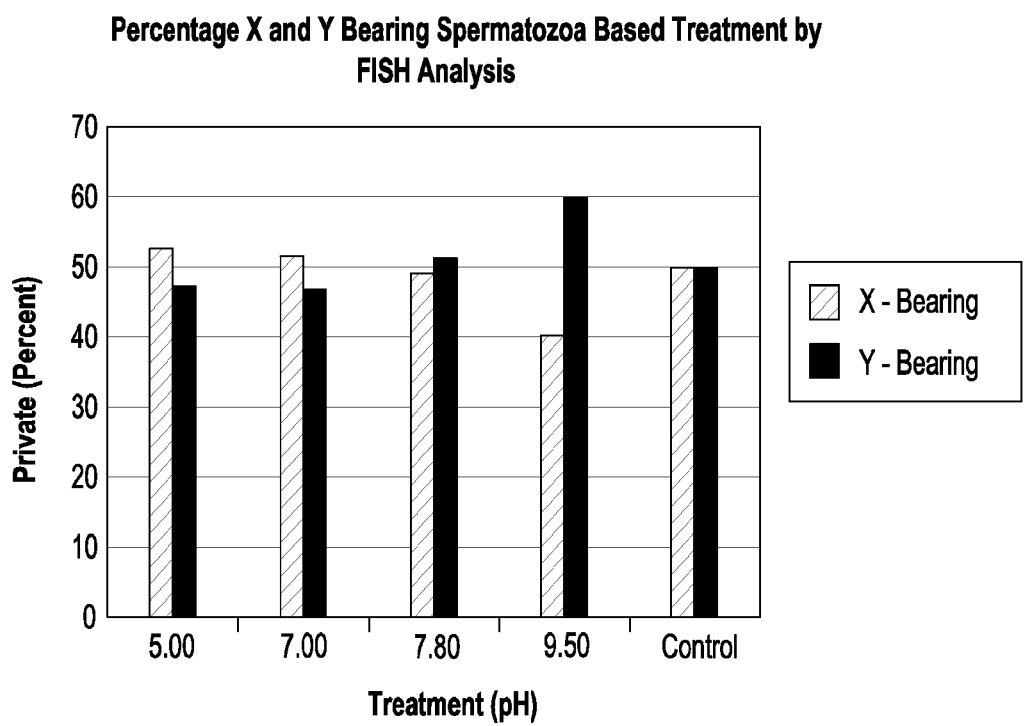
FIG. 16 is a chart of fluorescence in Situ Hybridization analysis of semen from each of the four pH environments of the Texas Tech University Semen Separator Chamber demonstrating a trend toward changes in X:Y ratios due to pH.

Samples for FISH were harvested at 6 hrs. To ensure harvested sample reflected the actual migration pattern, a plastic separator was used to seal the mesh basket and prevent fluid migration as it was removed from the chambers of the SSC. The FISH analysis indicated a trend (P=0.114) toward separation of X and Y bearing sperm. The greatest shift was detected in the 9.5 pH media which separated to a 40:60 ration for X:Y bearing spermatozoa, a 20% differential as compared to the almost 50:50 ratio of the control (FIG. 16). Other medias also indicate a possible shift, with the 5.0 media shifting 53:47 percent in favor of X bearing sperm, 7.0 media shifting slightly less a 52:48 in favor of X bearing sperm and 7.8 shifting 48:52 percent in favor of Y bearing sperm. This trend follows the long held theory that acidic conditions favor X bearing sperm and basic conditions favor Y bearing sperm [15, 16].

Statistical Analysis. All data demonstrated in different embodiments were initially analyzed using the general linear model of the Statistical Program for the Social Sciences. Data for media trials were collected in a completely randomized design with repeated measures over time. Using a two-way analysis of variance (ANOVA), data were analyzed for the effects of pH, time and a possible pH*time interaction. Data for semen trials were collected in a randomized complete block design, blocking by collection, with repeated measures over time. Using a two-way ANOVA, data were analyzed for differences in semen parameters (concentration, motility, and forward progressing), due to pH, time, and a possible pH*time interaction. In cases were the effects of the pH treatment were found to be independent of time, the data were re-analyzed using a one-way ANOVA and individual pH effects determined using Tukey's mean separation.

The present invention demonstrated about 20% shift from about 50:50 ratio to a about 40:60 ratio of X:Y bearing sperm shift the odds significantly in favor of having a male. In addition, the present invention provides an easy technique that can be performed with a minimum of equipment for gender selection based on pH.

In certain embodiments, the present invention describes the creation of an overall environment that presents each cell with several sub-environments simultaneously allowing the cell to migrate to its preferred location. The sub-environment is created by a chambered dish which has had a bio-compatible cell sifting basket, or equivalent mesh material seeded in the middle effectively creating, for example, a five chamber environment. Each outer chamber of the system is filled with a bio-compatible media of a pre-determined pH, for example ph 5, 7, 7.8 or 9.5. The charge of the mesh and static pressure will initially prevent movement of solutions thru the mesh. The size of the mesh opening will be of sufficient size to allow the passage of sperm cells of the specie being sorted, typically, but not limited to about 40~70 µm. The center well is filled with a mixture of a biocompatible of a predetermined pH (for example 7.4) and processed semen from a selected male animal. Filling of the center well will allow for minor exchange of ions between each of the outer chambers and the middle chamber described. The ion exchange will be sufficient to create pathways to attract cells to a preferred environment, and under the power of their own motility, cells will be attracted to one of the presented environments. Most importantly, the design of the system does not require that cells migrate thru suboptimal environments before arriving at the environment of choice.

In certain embodiments, the mesh material used in the present invention may be made by, but not limited to, nylon, gauze, paper, steel, polypropylene, cellulose, or combinations thereof. In another embodiment, each sub-environment chamber may be color coded to better identify each sub-environment. Yet in another embodiment, the present invention entails a method of sperm cell selection based upon pH, wherein individual sperm cells are presented with numerous pH environments almost simultaneously. Another embodiment encompasses a device with a minimum of three chambers separated by a biocompatible mesh material, which prevents the mass flow of fluid between chambers, but allows free movement of cells and slow movement of fluids between chambers. The design of chamber allows cells to select environment of choice based upon chemical interactions. The selection of environment based upon pH also separates cells by chromosome content, resulting in enhanced populations of X and Y bearing sperm.

Below is a table illustrating some of the reagent components used in the present invention:

TABLE 1

| Chemical | 100 mL | 500 mL | 800 mL | 1000 mL | 1500 mL |
|---|---|---|---|---|---|
| Calcium Carbonate Lactated Ringers for Semen Extender | | | | | |
| NaCl | .600 g | 3 g | 4.8 g | 6 g | 9 g |
| Na Lactate | .310 g | 1.55 g | 2.48 g | 3.1 g | 4.65 g |
| KCL | .030 g | .15 g | .24 g | .30 g | .45 g |
| Fuctose | .020 g | .1 g | .16 g | .2 g | .3 g |
| CaCO$_3$ | .040 g | .2 g | .32 g | .4 g | .6 g |
| Protein | 10% | 10% | 10% | 10% | 10% |
| Using liquid 50 mEq Na Lactate 1 ml = 560 mg | | | | | |
| NaCl | .600 g | 3 g | 4.8 g | 6 g | 9 g |
| Na Lactate | .55 mL | 2.75 mL | 4.4 mL | 5.50 mL | 8.3 mL |
| KCL | .030 g | .15 g | .24 g | .30 g | .45 g |
| Fuctose | .020 g | .1 g | .16 g | .2 g | .3 g |
| CaCO$_3$ | .040 g | .2 g | .32 g | .4 g | .6 g |
| Protein | 10% | 10% | 10% | 10% | 10% |
| Using liquid 60% Na Lactate syrup in water | | | | | |
| NaCl | .600 g | 3 g | 4.8 g | 6 g | 9 g |
| Na Lactate | .52 mL | 2.6 mL | 4.16 mL | 5.2 mL | 7.8 mL |
| KCL | .030 g | .15 g | .24 g | .30 g | .45 g |

TABLE 1-continued

| Chemical | 100 mL | 500 mL | 800 mL | 1000 mL | 1500 mL |
|---|---|---|---|---|---|
| Fuctose | .020 g | .1 g | .16 g | .2 g | .3 g |
| CaCO$_3$ | .040 g | .2 g | .32 g | .4 g | .6 g |
| Protein | 10% | 10% | 10% | 10% | 10% |

Protein Source. Protein Source. Combine a protein source, such as but not limited to human serum albumin, bovine serum albumin, synthetic serum substitutes, or non-animal sources such as soy flour or early sumac sorghum flour, or an extract of selected proteins from any of these sources, to provide the protein source for the extender. Liquid sources shall be added at the rate of 10% volume to volume of the extender base. Powder sources at 1.5 g per 100 ml of CaCO3 Lactated Ringers for Semen Extender, shake vigorously and warm in the water bath at least 30 minutes. Filter through several layers of gauze twice to remove sediment, add to extender at 10% of volume. Once protein source has been added to the extender, filter through a 0.45 µm nalgene filter and a 0.22 µm nalgene filter (i.e. 70 ml of protein source to 700 mL of extender).

In Semen Selection, a large volume of media was prepared in a batch and then aliquoted into 5 equal volumes each adjusted for pH with HCl and Ammonium Hydroxide as appropriate till the pH stabilized at 5.0, 7.0, 7.4, 7.8 and 9.5 respectively. These solutions were then refrigerated at least over night and allowed to return to room temperature before pH was again measured and solutions were allowed to warm to 37° C. before being added to the separation device.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Muehleis P M. Long S Y. 1976. The Effects of Altering the pH of Seminal Fluid on the Sex Ratio of Rabbit Offspring. Fertil. Steril. December; 27(12):1438-1445
2. Diasio R B, Glass R H. 1971. Effects of pH on the Migration of X and Y Sperm. Fertil. Steril. May; 22(5):303-5.
3. Downing D C, Donald M S, Black L, Carey W H, Delahanty D L. 1976. The Effect of Ion-Exchange Column Chromatography on Separation of X and Y Chromosome-Bearing Human Spermatozoa. Fertil. Steril. October; 27(10): 1187-1190.
4. Hossain A M, Barik S, Rizk B, and Thorneycroft I H. 1998. Preconceptional Sex Selection: Past, Present and Future. Arch. Androl. 40:3-14.
5. Rens W. Yang F, Welch G, Revell S, O'Brien P C M, Solanky N, Johnson L A, Ferguson Smith M A. 2001. An X-Y Paint Set and Sperm FISH Protocol that can be Used for Validation of Cattle Sperm Separation Procedures. Reproduction. 121:541-546.
6. Stolkowski J, Choukroun J. 1981. Preconception Selection of Sex in Man. Isr. J. Med. Sci. November; 17(11):1061-1067.

7. Johnson L A, Cran D G, Polge C. 1994. Recent Advances in Sex Preselection of Cattle: Flow Cytometric Sorting of X- and Y-Chromosome Bearing Sperm Based on DNA to Produce Progeny. Theriogenology. 41:51-56.
8. Johnson L A. 1995. Sex Preselection by Flow Cytometric Separation of X and Y Chromosome-bearing Sperm Based on DNA Difference: a Review. Reprod. Fertil. Dev. 7:893-903.
9. Blecher S R, Howie R, Li S, Detmar J, Blahut L M. 1999. A New Approach to Immunological Sexing of Sperm. Theriogenology. 52:1309-1321.
10. Maxwell W M C, Evans G, Hollinshead F K, Bathgate R, de Graaf S P, Eriksson B M, Gillan L, Morton K M, O'Brien J K. 2004. Integration of Sperm Sexing Technology into the ART Toolbox. Anim. Reprod. Sci. July; 82-83:79-95.
12. Kawarasaki T, Sone M, Yoshida M, Bamba K. 1996. Rapid and Simultaneous Detection of Chromosome Y- and 1-Bearing Porcine Spermatozoa by Fluorescence In Situ Hybridization. Mol. Reprod. Dev. April; 43(4):548-53.
13. Kibayashi J, Kohsaka T, Sasada H, Umezu M, Sato E. 1999. Fluorescence In Situ Hybridization with Y Chromosome-Specific Probe in Decondensed Bovine Spermatozoa. Theriogenology. 52:1034-1054.
14. Prien S D. 1991. A Comparative Study of Calcium Utilization in Human and Porcine Spermatozoa. PhD Diss., Texas Tech University., Lubbock, Tex.
15. Shettles L B. 1970. Factors Influencing Sex Ratios. Int. J. Gynecol Obstet. 8:643-647.
16. Muehleis P M. Long S Y. 1976. The Effects of Altering the pH of Seminal Fluid on the Sex Ratio of Rabbit Offspring. Fertil. Steril. December; 27(12):1438-1445.

What is claimed is:

1. A method for enriching X or Y-chromosome bearing sperm cells in a population, comprising the steps of:
   providing a separation vessel comprising a central chamber comprising a central chamber fluid at a physiological pH; an array of sub-chambers each having a sub-chamber fluid at a distinct pH; an array of individual channels connecting the array of sub-chambers to the central chamber; and a biocompatible mesh separating the array of individual channels from the central chamber to allow free movement of a sperm cell and slow movement of fluids between the central chamber and the array of sub-chambers;
   allowing each of the sub-chamber fluids to contact the central chamber fluid;
   placing a population of sperm cells comprising X-chromosome sperm cells and Y-chromosome sperm cells in the central chamber, wherein the population of sperm cells simultaneously contact each of the sub-chamber fluids that are at a distinct pH;
   allowing the X-chromosome sperm cells to migrate to a first sub-chamber of the array of sub-chambers based on a pH preference;
   allowing the Y-chromosome sperm cells to migrate to a second sub-chamber of the array of sub-chambers based on a pH preference,
   wherein migration based upon pH separates cells by chromosome content, resulting in enhanced populations of X-chromosome and Y-chromosome bearing sperm;
   collecting the enhanced populations of X-chromosome sperm cells from the first sub-chamber; and
   collecting the enhanced populations of Y-chromosome sperm cells from the second sub-chamber.

2. The method of claim 1, wherein the biocompatible mesh comprise openings of about 40-70 μm.

3. The method of claim 1, wherein the biocompatible mesh permits sufficient minor exchange of ions to permit mobility pathways for sperm cells.

4. The method of claim 1, wherein the biocompatible mesh prevent mass flow of fluid between the chambers, but allows free movement of sperm cells and slow movement of fluids between chambers.

5. The method of claim 1, wherein each of the sub-chamber fluids have a different pH wherein the pH is 5, 6, 7, 7.5, 7.8, 8, 8.5, 9 or 9.5.

6. The method of claim 1, wherein the biocompatible mesh comprises an electrostatic charge, static pressure, or both that prevent movement of the solutions through the mesh.

7. The method of claim 1, wherein the population of sperm cells, the central chamber fluid, the sub-chamber fluid or a combination thereof further comprise a thixotropic agent.

8. The method of claim 1, wherein the biocompatible mesh openings are customized to the size of the sperm sorted.

9. The method of claim 1, further comprising the step of collecting the X-chromosome sperm cells, the Y-chromosome sperm cells or both from one or both sides of the interface between the biocompatible mesh.

* * * * *